(12) United States Patent
Chien

(10) Patent No.: US 12,369,987 B2
(45) Date of Patent: Jul. 29, 2025

(54) SELF-LOCATING, ACTIVE MARKERS FOR NAVIGATED, AUGMENTED REALITY, OR ROBOTIC SURGERY

(71) Applicant: Pacific Medical Device Consulting LLC, Vashon, WA (US)

(72) Inventor: Dennis Chien, Vashon, WA (US)

(73) Assignee: PACIFIC MEDICAL DEVICE CONSULTING LLC, Vashon, WA (US)

( * ) Notice: Subject to any disclaimer, the term of this patent is extended or adjusted under 35 U.S.C. 154(b) by 0 days.

(21) Appl. No.: 17/228,841

(22) Filed: Apr. 13, 2021

(65) Prior Publication Data

US 2022/0175460 A1 Jun. 9, 2022

Related U.S. Application Data

(60) Provisional application No. 63/123,383, filed on Dec. 9, 2020.

(51) Int. Cl.
*A61B 34/20* (2016.01)
*A61B 8/08* (2006.01)
(Continued)

(52) U.S. Cl.
CPC ............ *A61B 34/20* (2016.02); *A61B 8/0841* (2013.01); *A61B 34/30* (2016.02); *A61B 90/39* (2016.02);
(Continued)

(58) Field of Classification Search
CPC . A61B 34/20; A61B 90/39; A61B 2034/2048; A61B 2034/2063;
(Continued)

(56) References Cited

U.S. PATENT DOCUMENTS

| 6,662,036 B2 | 12/2003 | Cosman |
| 7,166,114 B2 | 1/2007 | Moctezuma et al. |

(Continued)

FOREIGN PATENT DOCUMENTS

| CA | 2701238 A1 * | 4/2009 | ........... A61F 13/023 |
| EP | 3498212 A1 * | 6/2019 | ............ A61B 34/20 |

(Continued)

OTHER PUBLICATIONS

Cambridge University Press & Assessment. (n.d.). Where. Cambridge Dictionary. https://dictionary.cambridge.org/us/grammar/british-grammar/where#google_vignette (Year: 2023).*

(Continued)

*Primary Examiner* — Ashley K Buran
*Assistant Examiner* — Helene Bor
(74) *Attorney, Agent, or Firm* — Perkins Coie LLP

(57) ABSTRACT

Self-locating active markers (SLAMs) can locate themselves with respect to patient's internal anatomy and be physically located and visible in an operating room (OR) coordinate space, which can increase precision of co-registration between augmented reality (AR) systems and medical imaging. Each SLAM may include 9-axis accelerometers and ultrasound technology to locate themselves by orientation and distance to internal skeletal and/or soft tissue anatomy. Multiple SLAMS affixed to skin near operative site at a location visible to a surgical navigation system and/or the surgeon's AR Headset during a procedure may report relative distance changes between their location and internal skeletal anatomy in order to maintain surgical navigation system or AR coordinate system co-registration to the imaged internal coordinate systems. Sequential time of flight calculations from ultrasound array alone or in combination with 9-axis accelerometer data may be used.

16 Claims, 13 Drawing Sheets

(51) Int. Cl.
  *A61B 34/30* (2016.01)
  *A61B 90/00* (2016.01)
(52) U.S. Cl.
  CPC ............... *A61B 2034/2048* (2016.02); *A61B 2034/2063* (2016.02); *A61B 2090/365* (2016.02); *A61B 2090/3929* (2016.02)
(58) Field of Classification Search
  CPC ............ A61B 2090/3929; A61B 34/30; A61B 8/0841; A61B 2090/365
  See application file for complete search history.

(56) References Cited

U.S. PATENT DOCUMENTS

| | | | |
|---|---|---|---|
| 9,173,715 | B2 | 11/2015 | Baumgartner |
| 9,439,662 | B2 | 9/2016 | Hirszowicz et al. |
| 9,498,647 | B2 | 11/2016 | Kantrowitz et al. |
| 9,928,629 | B2 | 3/2018 | Benishti et al. |
| 9,978,141 | B2 | 5/2018 | Stolka et al. |
| 10,016,243 | B2 | 7/2018 | Esterberg |
| 10,134,166 | B2 | 11/2018 | Benishti et al. |
| 10,282,913 | B2 | 5/2019 | Kellogg et al. |
| 10,382,748 | B2 | 8/2019 | Benishti et al. |
| 10,535,160 | B2 | 1/2020 | Kellogg et al. |
| 10,575,906 | B2 | 3/2020 | Wu |
| 10,788,672 | B2 | 9/2020 | Yadav et al. |
| 10,799,296 | B2 | 10/2020 | Lang |
| 11,026,598 | B2 | 6/2021 | Van De Vyver |
| 11,250,726 | B2 * | 2/2022 | Barral .................. G09B 23/285 |
| 11,298,186 | B2 * | 4/2022 | Chou .................. A61B 17/3423 |
| 2008/0021310 | A1 * | 1/2008 | Amiot .................... A61B 34/20 606/151 |
| 2010/0152616 | A1 * | 6/2010 | Beyhan ................ A61B 10/025 600/568 |
| 2015/0173715 | A1 | 6/2015 | Raghavan et al. |
| 2016/0225192 | A1 * | 8/2016 | Jones ....................... G06F 3/017 |
| 2017/0079723 | A1 * | 3/2017 | Fleig ...................... A61B 34/20 |
| 2017/0178375 | A1 | 6/2017 | Benishti et al. |
| 2017/0245830 | A1 * | 8/2017 | Netravali ............... A61B 34/20 |
| 2018/0182150 | A1 | 6/2018 | Benishti et al. |
| 2018/0279913 | A1 * | 10/2018 | Frasier .................. A61B 6/545 |
| 2019/0026922 | A1 | 1/2019 | Kellogg et al. |
| 2019/0026948 | A1 | 1/2019 | Kellogg et al. |
| 2019/0043238 | A1 | 2/2019 | Benishti et al. |
| 2019/0090955 | A1 * | 3/2019 | Singh ..................... A61B 17/00 |
| 2019/0117318 | A1 | 4/2019 | Charron et al. |
| 2019/0175228 | A1 | 6/2019 | Elimelech et al. |
| 2019/0192230 | A1 | 6/2019 | Siemionow et al. |
| 2019/0231443 | A1 * | 8/2019 | McGinley ............. A61B 90/06 |
| 2019/0273916 | A1 | 9/2019 | Benishti et al. |
| 2019/0380792 | A1 * | 12/2019 | Poltaretskyi .......... A61B 34/25 |
| 2020/0022774 | A1 * | 1/2020 | Douglas ................ A61B 90/37 |
| 2020/0163723 | A1 | 5/2020 | Wolf et al. |
| 2020/0163739 | A1 | 5/2020 | Messinger et al. |

FOREIGN PATENT DOCUMENTS

| | | | |
|---|---|---|---|
| WO | WO-2012109361 A3 * | 11/2012 | ............. A61B 34/20 |
| WO | 2019245848 A1 | 12/2019 | |
| WO | WO-2020247619 A1 * | 12/2020 | ......... A61B 18/1492 |

OTHER PUBLICATIONS

Ibrahim AlMohimeed et al, "Development of wearable and flexible ultrasonic sensor for skeletal muscle monitoring," 2013 IEEE International Ultrasonics Symposium (IUS), Prague, Czech Republic, 2013, pp. 1137-1140 (Year: 2013).*

He, Changyu et al., "Inertial and optical sensor fusion to compensate for partial occlusions in surgical tracking systems," Proc. SPIE 9618, 2015 International Conference on Optical Instruments and Technology: Optical Systems and Modern Optoelectronic Instruments, 961802 (Aug. 5, 2015) (Year: 2015).*

* cited by examiner

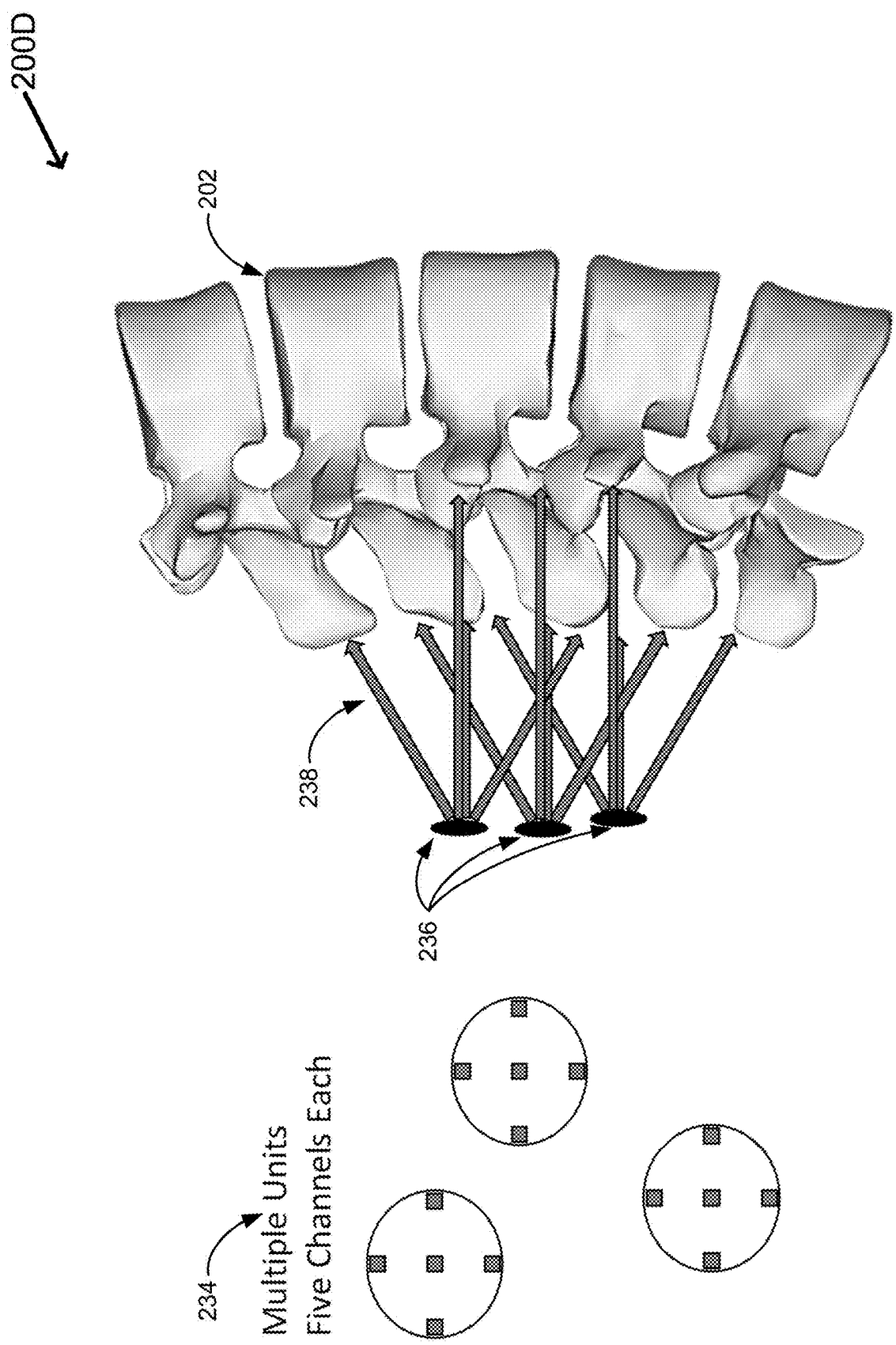

SELF-LOCATING, ACTIVE MARKERS FOR NAVIGATED, AUGMENTED REALITY, OR ROBOTIC SURGERY

CROSS REFERENCE TO RELATED APPLICATIONS

This application claims the benefit of U.S. Provisional Patent Application Ser. No. 62/123,383 filed on Dec. 9, 2020. The disclosures of the above applications are hereby incorporated by reference for all purposes.

BACKGROUND

Unless otherwise indicated herein, the materials described in this section are not prior art to the claims in this application and are not admitted as prior art by inclusion in this section.

Surgical access to structures not visible from outside the body can be accomplished in two main ways: Surgery where direct visualization of the target site is achieved by opening skin layers, separating or moving muscle groups or organs, removing tissue, and so forth until the target site is directly visualized. The amount of access can depend on the amount of visualization required, the specific anatomy, the size of the instruments and implants required to perform the surgery.

Surgery can also be accomplished without direct visualization by using non-invasive imaging information. For example, a live or near live X-ray view may be used to guide radio-opaque instruments and implants while visualizing internal organs and skeletal structure. This is typically accomplished using intraoperative C-Arm (X-ray) used in single shots, or continuous "fluoro" mode, or 360 scans. These methods expose the patient to significant levels of radiation. The methods also expose the surgical staff to radiation even when proper lead protective gear is worn from reflected radiation. Staff that receive even low doses of radiation during surgery can be at risk because of the effects of repeated exposures.

Taking intraoperative C-Arm images carries other burdens such as time to take the image. Qualified C-Arm technicians are often shared between operating room (OR) theaters and surgery can be delayed waiting for a technician to be available. Images may require a reconfiguration of the surgical field for the C-Arm (e.g. filling the wound with saline for contrast, removing retractor hardware, covering the wound to reduce risk of infection, etc.). Further challenges may include challenges accessing the area. In some surgeries, the surgeon needs to remain in the location where the C-Arm would need to be (e.g., Spinal Pedicle Subtraction Osteotomy during the spinal manipulation to close the osteotomy, a C-Arm view to show the angle of closure would be desired, but the surgeon cannot step out to allow the C-Arm access because of the active bleeding from the osteotomy).

In Navigated/AR/Robotic surgery, X-ray exposure is reduced to the patient and staff during the procedure by utilizing pre-operative imaging of the patient to guide the surgeon's access paths for instruments through tissue to the target site for surgery. The access paths are challenged in several ways which include: Finding the right entry point, end point, and path of approach for the instrument, having the path avoid transecting or putting pressure on specific anatomy such as vessels, nerves, organs, or bony anatomy.

While augmented reality (AR) heads up display/headset/3D projection surgery technology (referred to generically as AR Headset going forward) is addressed herein specifically, the principles are applicable to see through navigated, robotically assisted surgery, or any method that seeks to co-register internal and external coordinate systems for the purpose of guiding the surgical procedure (referred to generically as AR System going forward). Implementation of an AR System in surgery involves co-registration of multiple 3D coordinate systems primarily grouped into internal (inside the patient) and external (the operating room or outside the body in general).

A major difficulty in co-registering internal and external coordinate systems lies in the creation of a non-invasive accurate and continuous co-registration. Through such a co-registration, it is possible to overlay 3D visualization from pre-operative imaging of internal structures in the surgeon's AR view of the patient. With such a visualization, the surgeon is able to manipulate instruments that penetrate the skin and tissues through an AR generated, visually informed path. Conventional approaches include co-registration using skin tags. Skin tags are visually trackable within the OR space. Tags may be retroreflective, or active emitters into the OR space (e.g. IR flashing, RF emission). They maybe calibrated to an AR System to the OR space through their sequential identification with a probe, or visually from a tracking system in the OR. Skin tags that are placed, or locations that are marked on the patient during the pre-operative imaging can be used as fiducial points to co-register internal and external space. The main challenge with using skin tags are: 1) they can move with respect to internal anatomy during the operation; and 2) when used as fiducials in pre-operative imaging inaccuracies occur because skin locations can be different with respect to internal anatomy or each other because of different body positions or orientation during the surgical procedure with regard to the position(s) of the pre-operative imaging.

The space may be co-registered to an internal landmark through intraoperative X-ray guided or manual surgical access to that landmark with an instrument that protrudes to the OR space in a way visible to the tracking system in the OR. Conventional approaches also include bone clamps. Bone clamps are attached to known internal anatomy through surgical access to that landmark either manually with direct visualization, manually without guidance, or guided by intraoperative X-ray. The protruding element of the bone clamps, visible outside the skin, are tracked and co-registered to the OR space using conventional surgical navigation techniques. A portion of the bone clamp protrudes from the surgical wound for the duration of the operation. It causes a larger or additional incision than would not otherwise be necessary and can limit surgeon's access to areas of interest. Repositioning the bone clamp to gain access consumes OR time and increases time of anesthesia for the patient.

To summarize, implementation of navigated, or augmented reality, or robotics in surgery necessitates co-registration of multiple 3D coordinate systems. A major difficulty lies in maintaining an accurate and continuous co-registration of the external coordinate system used to track instruments in the operating room (with parts of instruments penetrating the patient) with the internal coordinate system in which the pre-operative medical imaging is stored. Minimally invasive surgery limits access to internal landmarks of the skeletal and other imaged anatomy. Mechanical arrays attached to internal bone anatomy have been utilized to bridge the two 3D coordinate systems. Non-invasive skin markers can provide limited association but are not stable relative to other internal landmarks from patient positioning, and skin movement during the operation.

SUMMARY

The present disclosure generally describes methods and apparatuses associated with self-locating, active markers (SLAMs) for navigated, augmented reality, or robotic surgery.

Self-locating active markers may locate themselves, continuously and in real time, with respect to patient's internal anatomy and be physically located and visible in the OR coordinate space, which may increase the precision of existing systems or provide independent co-registration between the AR Systems and the medical imaging. Each SLAM is enabled with ultrasound technology, and optionally 9-axis accelerometers, and may accurately locate itself by orientation and distance to internal skeletal and/or soft tissue anatomy. A number of SLAMs are affixed to the skin near the operative site in a location that is visible to the AR System and/or the surgeon's AR Headset during the planned procedure. The SLAM reports relative distance changes between its location and internal skeletal anatomy in order to maintain surgical navigation system or augmented reality coordinate system co-registration to the imaged internal coordinate systems. Data from multiple SLAM units are combined to create a profile of internal structures. Arrangement of SLAM units in uniform patterns will simplify profile reconstruction but is not strictly required. Sequentially sampled time of flight calculations from ultrasound transceivers alone or in combination with 9-axis accelerometer data may be used. Additionally, the 9-axis accelerometer data may be used for inertial tracking and may calculate angular and position offsets from last known position in a backup role to the optical tracking system. Communication with an integrating computer may be by IR frequencies, BT, WiFi, RF, dynamic QR code, etc.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 2A through 2D illustrate example configurations of single and multiple SLAMs with single or multiple channels;

DETAILED DESCRIPTION

Figure 1:
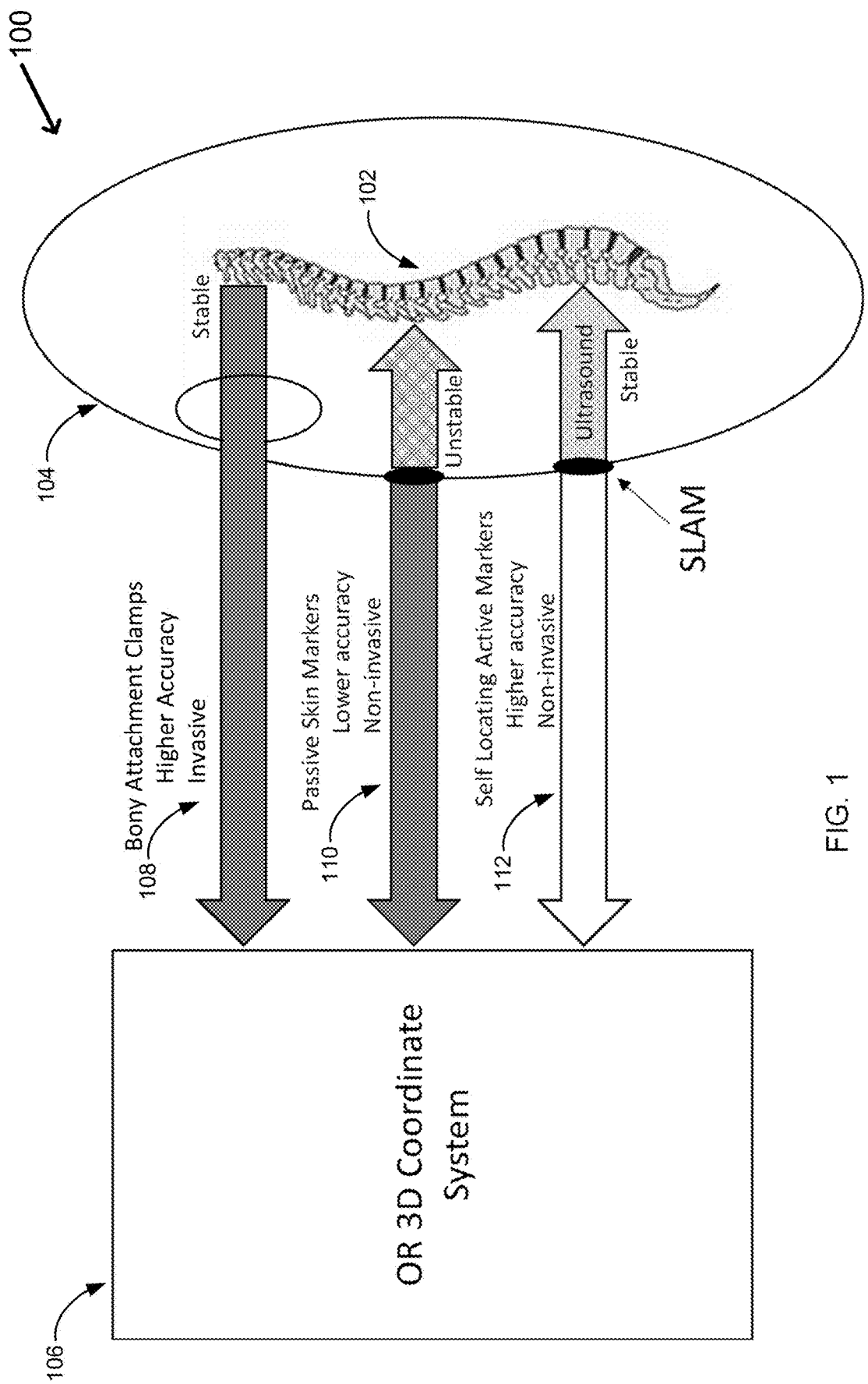
FIG. 1 illustrates conceptually a comparison of conventional approaches and SLAMs.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems and/or devices associated with self-locating, active markers (SLAMs) for navigated, augmented reality, or robotic surgery.

FIG. 1 illustrates conceptually a comparison of conventional approaches and SLAMs. All three example systems provide internal structure 102 (e.g., bone structure) information to an OR coordinate system 106 as shown in diagram 100. Bone attachment clamps 108 are stable and provide high accuracy internal structure location. However, they are invasive and are associated with all disadvantages and risks of invasive surgery. Passive skin markers 110 are (removably) attached to the skin 104 and are non-invasive. However, they may be unstable with respect to the position of internal structures and each other and provide lower accuracy in locating internal structures. SLAMs 112 may also be removably attached to the skin 104 and are non-invasive. Unlike the passive skin markers 110, SLAMs 112 may provide higher accuracy in locating internal structures through ultrasound detection of such structures.

Figure 2A:
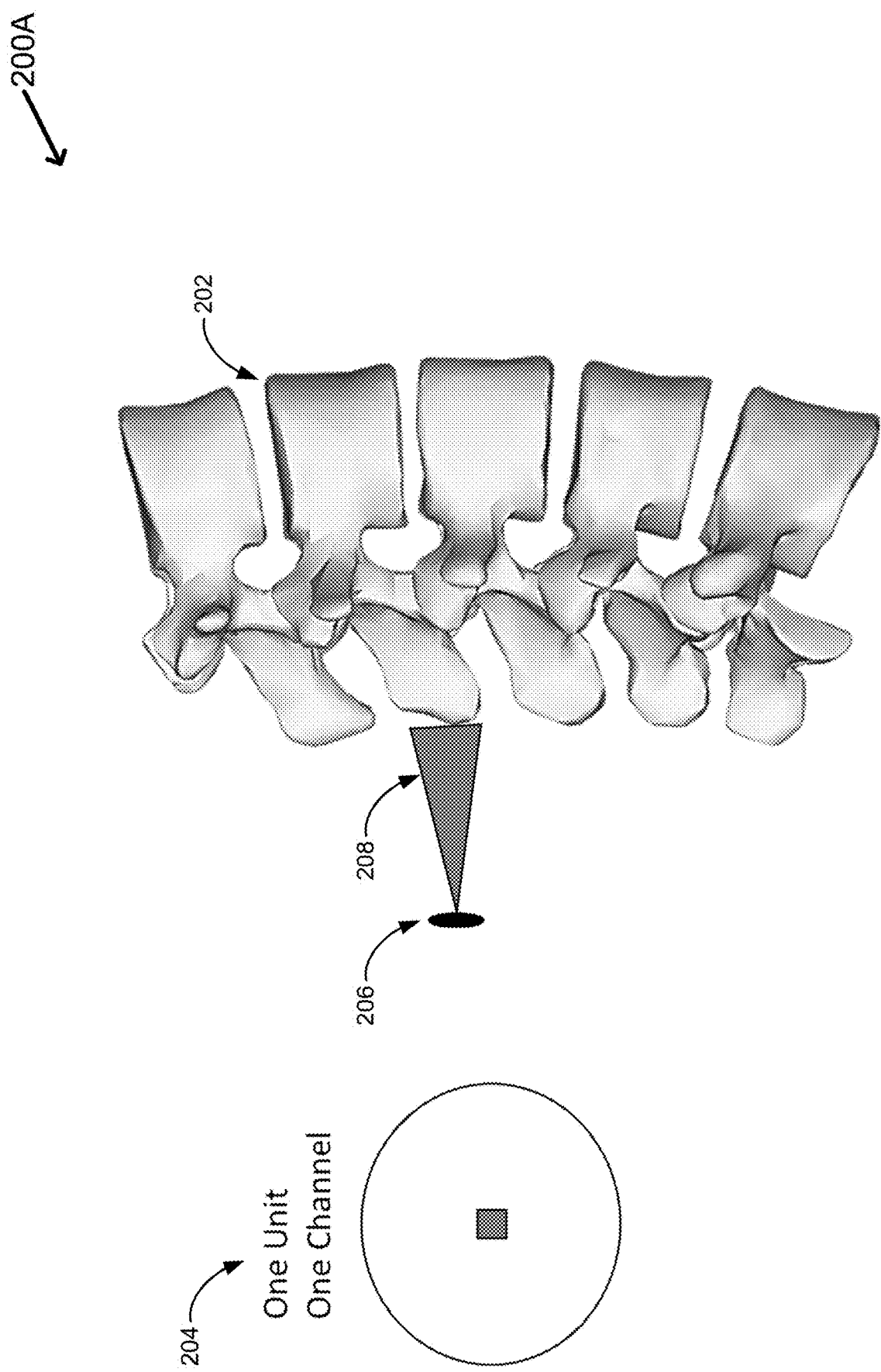
Figure 2B:
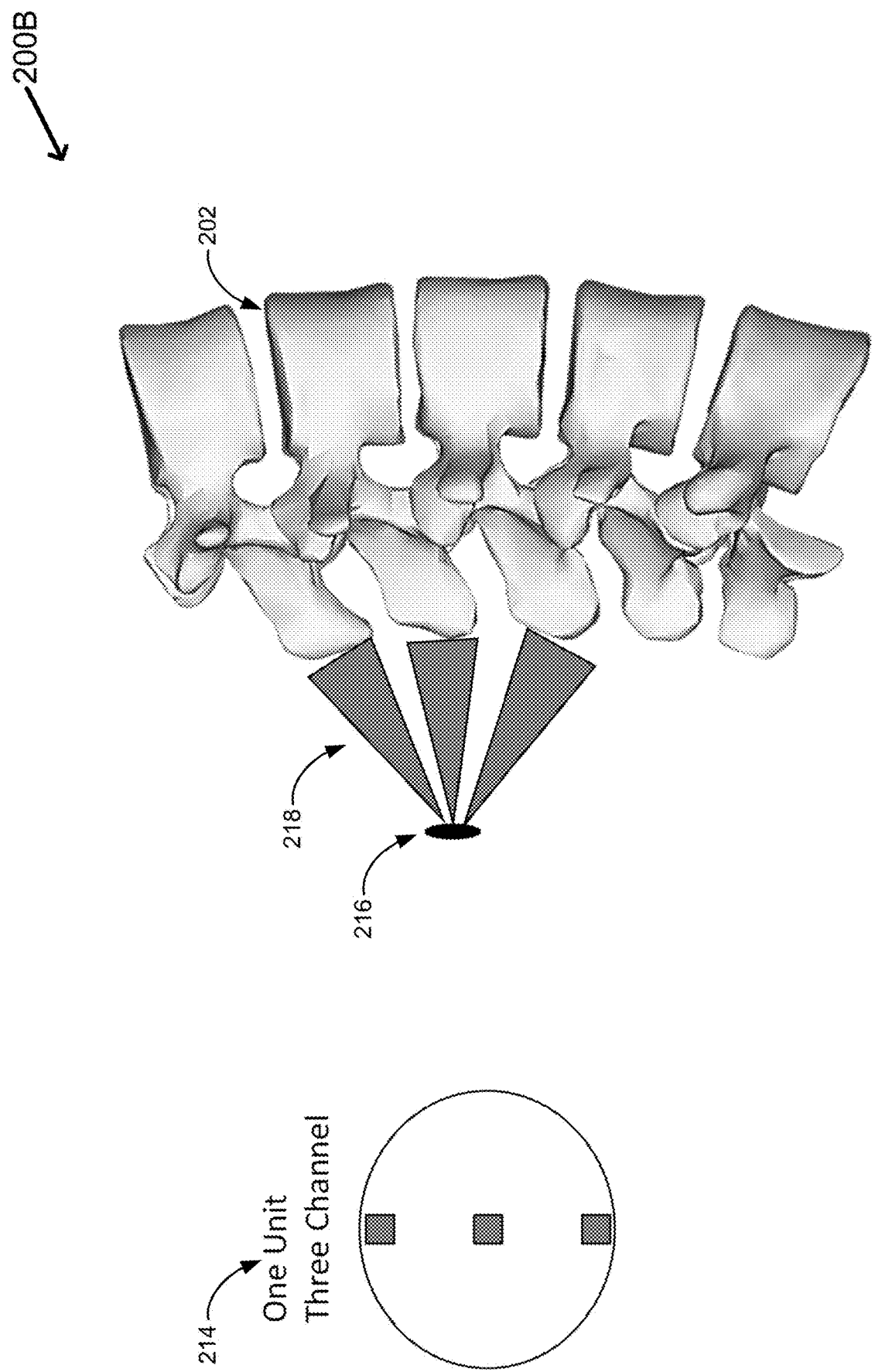
Figure 2C:
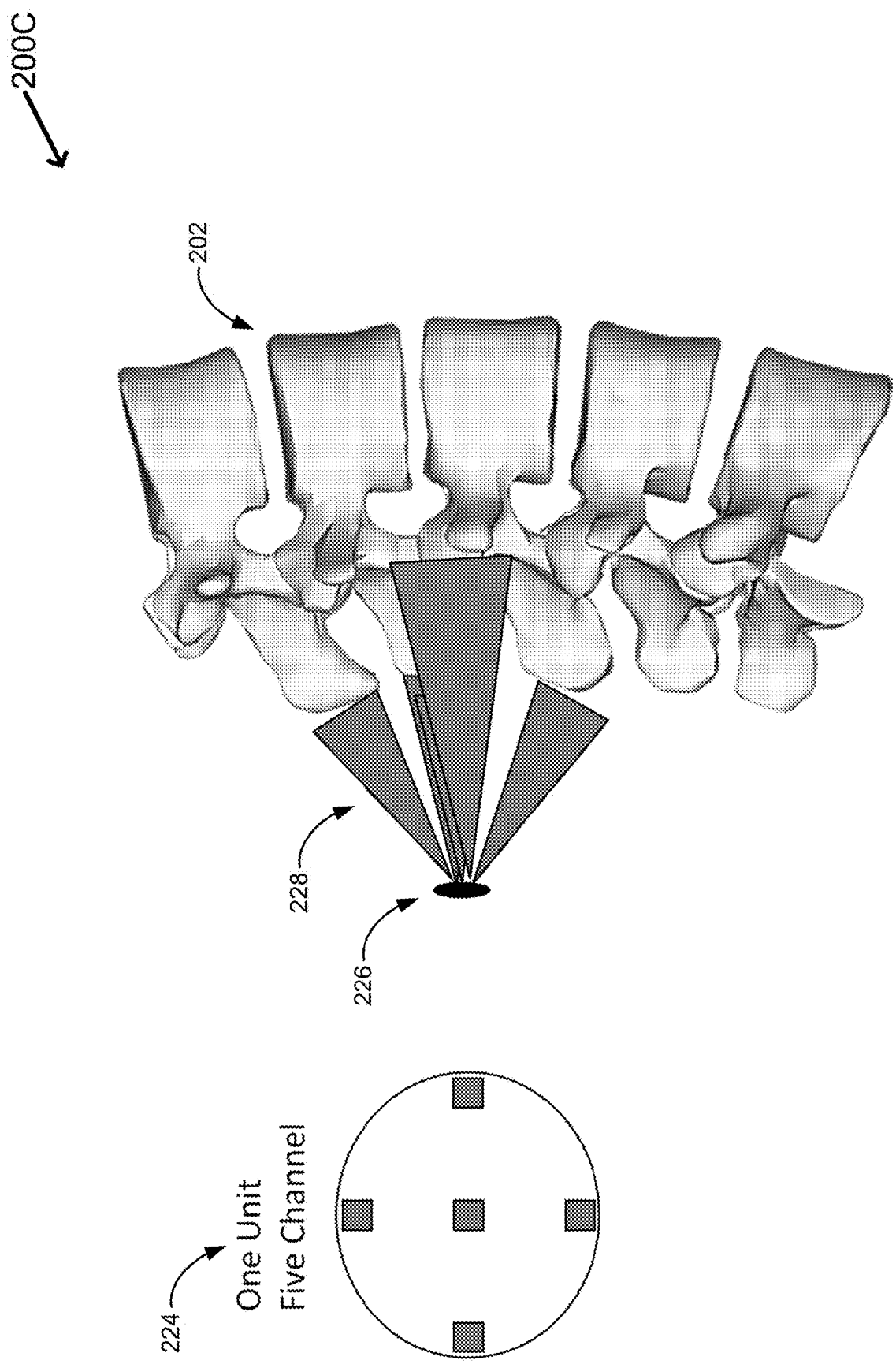

FIG. 2A through 2D illustrate example configurations of single and multiple SLAMs with single or multiple channels. Diagram 200A of FIG. 2A shows an example one unit, one channel system 204, where the single SLAM 206 may use ultrasound detection 208 to locate internal (bone) structure 202. Diagram 200B of FIG. 2B shows an example one unit, three channel system 214, where the single SLAM 216 may use three separate transducers for ultrasound detection 218 to locate internal (bone) structure 202. Diagram 200C of FIG. 2C shows an example one unit, five channel system 224, where the single SLAM 226 may use five separate transducers for ultrasound detection 228 to locate internal (bone) structure 202. Diagram 200D of FIG. 2D shows an example three unit, five channel system 234, where each of the three SLAMs 236 may use five separate transducers for ultrasound detection 238 to locate internal (bone) structure 202. The example configurations in FIG. 2A through 2D are for illustration purposes only and any combination of number of SLAMs and transducers aimed at any angle may be used to detect location of internal structures. Higher number of transducers/SLAMs may provide higher accuracy in internal structure profile reconstruction mediated by spatial sampling theory and the Nyquist-Shannon sampling theorem.

Self-Locating Active Markers (SLAMs) that may locate themselves, in real time, with respect to patient's internal anatomy and be located in the OR coordinate space may increase the precision of co-registration between the AR Systems and the pre-operative medical imaging. Each SLAM may be enabled with ultrasound technology and optionally, 9-axis accelerometers and may accurately locate themselves by orientation and distance to internal skeletal anatomy (and soft tissue anatomy).

SLAMs may also use other non-invasive probing energy to locate themselves with respect to internal anatomy such as light. SLAMs may use a probing energy that reflects from internal structures and is then detected. SLAMs may use a probing energy that causes some state change in internal structures that makes that change detectible through a non-invasive means. SLAMs may locate a selected difference in internal structure detectability caused by a treatment. That treatment may cause a detectable reaction from a probing signal (e.g., ultrasound detection of microbubble accumulation in cancer cells) or a detectable location using external detection (radioisotope markers). SLAMs may use a probing energy that reflects from materials introduced into the body (detectable by probing energy) that distributes in anatomically selective ways (e.g., injection of microbubbles in interfacial layers, radio opaque dye in the bloodstream). These modalities may be used alone or in combination.

SLAMs may be used to co-register an OR coordinate system with the internal coordinate system of any pre or intraoperative 2D or 3D or 4D (3D motion in time) image data such as but not limited to: CT, MRI, X-Ray, Neurography, Angiography, PET, SPECT, CT/PET, Ultrasound. SLAM co-registration may be associated with any system that makes use of a coordinate system in the operating room environment to track objects such as but not limited to surgical instruments, AR Headsets, implants, surgeon limbs, surgeon fingers; and uses techniques including but not limited to AR Systems, Computer Guided/Navigated Surgery, or Robotic Surgery.

In one embodiment appropriately compatible SLAMs are placed prior to pre-operative scans. They may be sterilizable. They may have adhesive holding the SLAM to the skin, and gel captured between the SLAM and the skin. This may create fiducials during scans and simplifies calibration during surgery. In another embodiment a Navigation system or AR Headset may be grossly calibrated to patient aiming at observable anatomy (e.g. the head and feet) or with human entry by any conventional interface such as but not limited to Voice, Eye movement, Head movement, controller, keyboard, etc. SLAMs may be placed after patient positioning. SLAM calibration may be performed, scan information merged with pre-operative image data and gross position provided by AR Headset observing SLAM placement. SLAM calibration may be performed in a similar manner to conventional skin tags utilizing tracked marker probes to locate and calibrate each tag one at a time. During the surgery, relative changes in position of tags to the internal anatomy may be communicated to the AR System.

Figure 3:
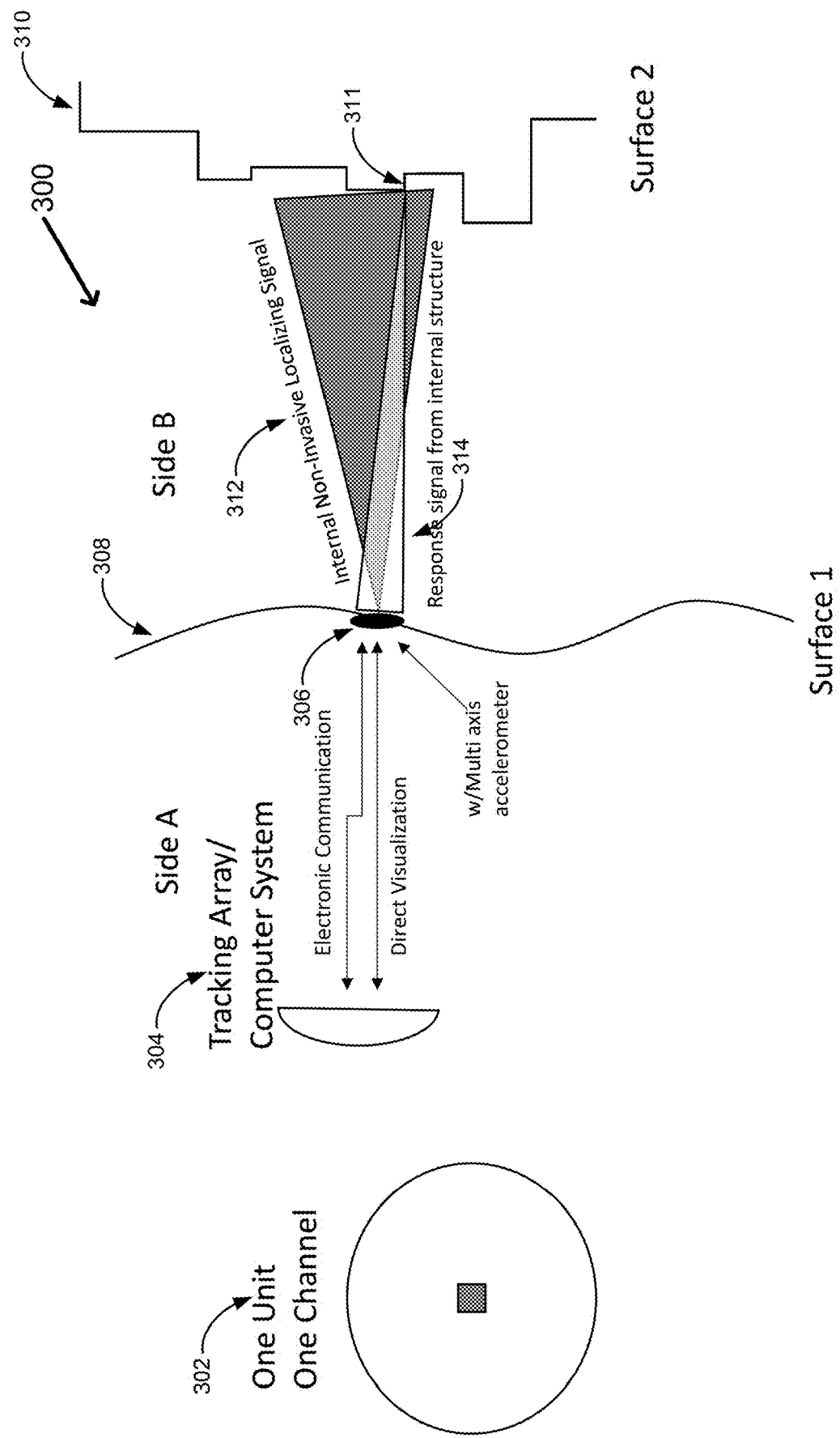
FIG. 3 illustrates operation of an example single unit, single channel system in detecting internal structures being tracked and communicating with an AR System tracking array/computer system.

FIG. 3 illustrates operation of an example single unit, single channel system in detecting internal structures being tracked and in communicated with a tracking array/computer system. Diagram 300 shows a one unit, one channel system 302 implemented using a single channel SLAM 306 attached to the skin 308 of a patient and detecting the surface of the nearest reflective internal structure 311 by transmitting a narrow focused localizing signal 312 toward the internal structure 311 and receiving reflected response signal 314 from the internal structure 311. The SLAM 306 may be in communication (wired or wireless) with a tracking array/computing system 304 to receive instructions (e.g., when to transmit) and to provide the detected response signal. Time of flight information may be used to determine the distance from the SLAM 306 to the internal structure 311. To help in locating the SLAM, the SLAM 306 may also be directly visible by the tracking array/computing system 304. In some examples, the SLAM 306 may include a multi-axis accelerometer to assist in location.

Figure 4:
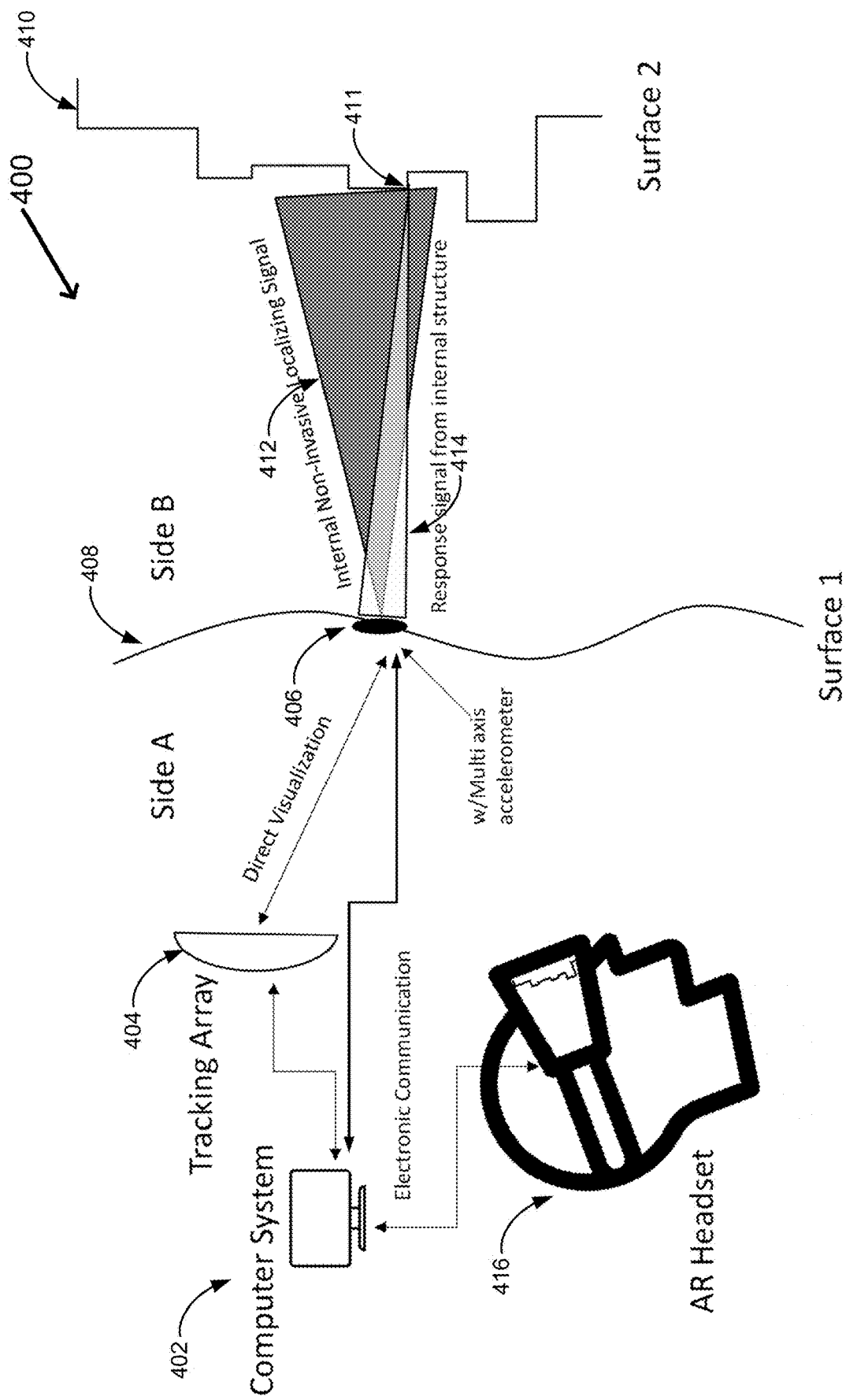
FIG. 4 illustrates operation of an example single unit, single channel system with monitoring components in detecting internal structures.

FIG. 4 illustrates operation of an example single unit, single channel system with AR System monitoring components in detecting internal structures. Diagram 400 shows a one unit, one channel system implemented using a single channel SLAM 406 attached to the skin 408 of a patient and detecting the surface of the nearest reflective internal structure 411 by transmitting a narrow focused localizing signal 412 toward the internal structure 411 and receiving reflected response signal 414 from the internal structure 411. Time of flight information may be used to determine the distance from the SLAM 406 to the internal structure 411. The SLAM 406 may be in communication (wired or wireless) with a computing system 402 and a tracking array 404. The computing system 402 may generate a profile of the internal structure 410 based on received information from the SLAM 406 and provide the profile information to an AR Headset 416 to be displayed in conjunction with the OR coordinate system (e.g., to a surgeon). To help in locating the SLAM, the SLAM 406 may also be directly visible to the tracking array 404. In some examples, the SLAM 406 may include a multi-axis accelerometer for self-location.

Figure 5:
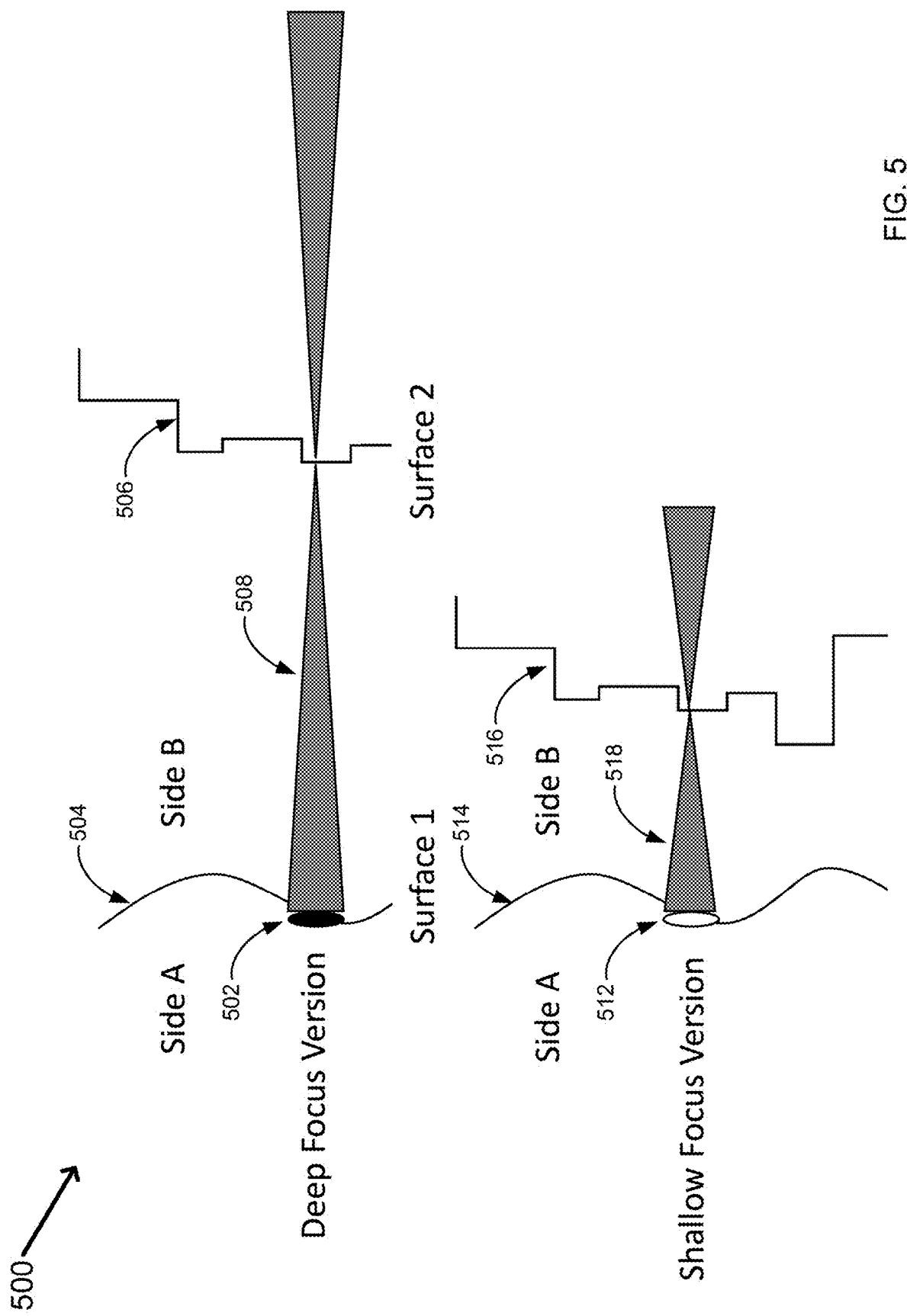
FIG. 5 illustrates conceptually a comparison between deep focus and shallow focus versions of an example SLAM.

FIG. 5 illustrates conceptually a comparison between deep focus and shallow focus versions of an example SLAM. Depending on application, different types of SLAMs may be used in implementation. For example, to best detect and locate bone structure close to the skin (e.g., vertebrae of a low BMI patient) a shallow focus SLAM may be used and to best detect and locate deeper bone structure (e.g., vertebrae of a high BMI patient) a deep focus SLAM may be used. By avoiding use of a single focus SLAM for a variety of bone structures, higher accuracy may be attained in detecting and locating the bones. Diagram 500 shows a deep focus version SLAM 502 attached to skin 504 and using deep focus ultrasound detection 508 to detect a profile of deep bone structure 506. The diagram, also shows a shallow focus SLAM 512 attached to skin 514 and using shallow focus ultrasound detection 518 to detect a profile of shallow bone structure 516. It is envisioned that a SLAM may be tunable to optimize signals at different distances.

Figure 6:
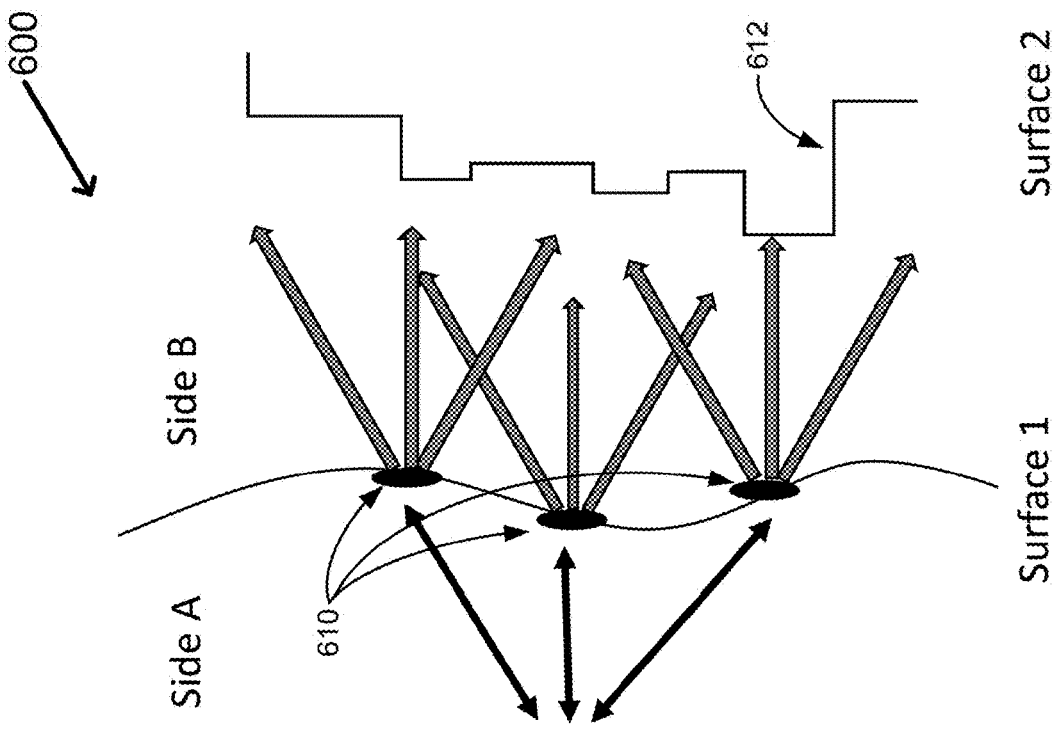
FIG. 6 illustrates an example pre-procedure and procedure profile matching through an example three unit, three channel system.
Figure 6:
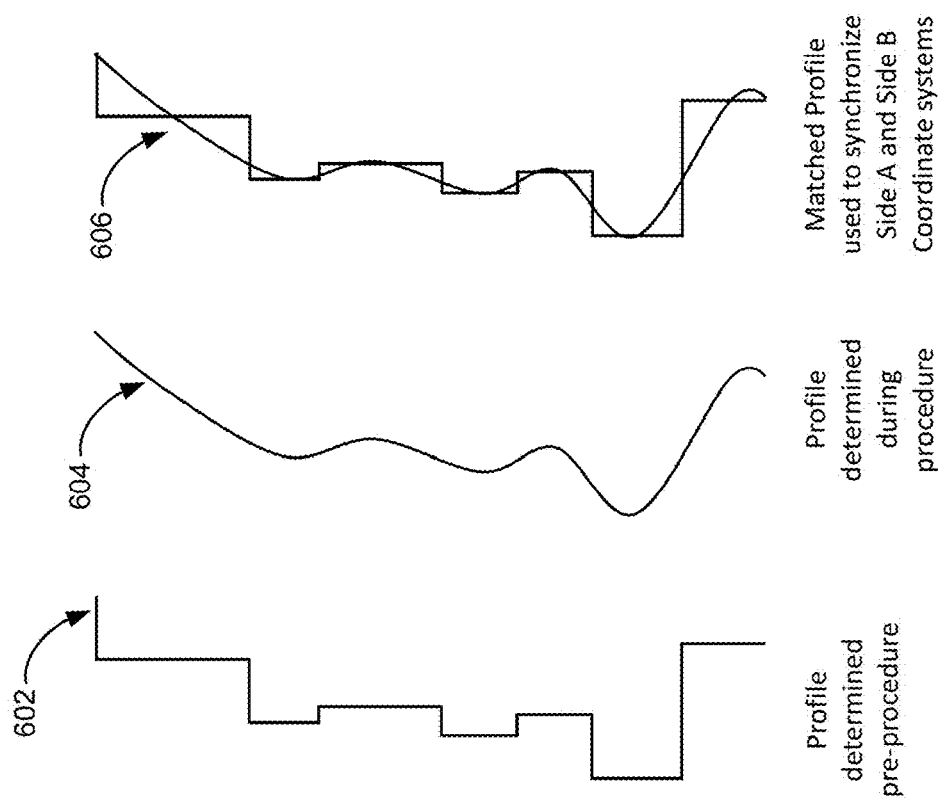

FIG. 6 illustrates a 2-dimensional example of pre-procedure and procedure profile matching through an example three unit, three channel sub-system. 3-dimensional extension of the technique is envisioned. Diagram 600 shows how a bone structure profile determined pre-procedure (602) and a profile determined during procedure (604) may be combined to a best fit matched profile to synchronize side A (OR) and side B (internal) coordinate systems. The diagram also shows the system to detect the internal coordinate profile 612. The system includes a tracking array 608 monitoring three SLAMs 610, each with three transducers.

Figure 7:
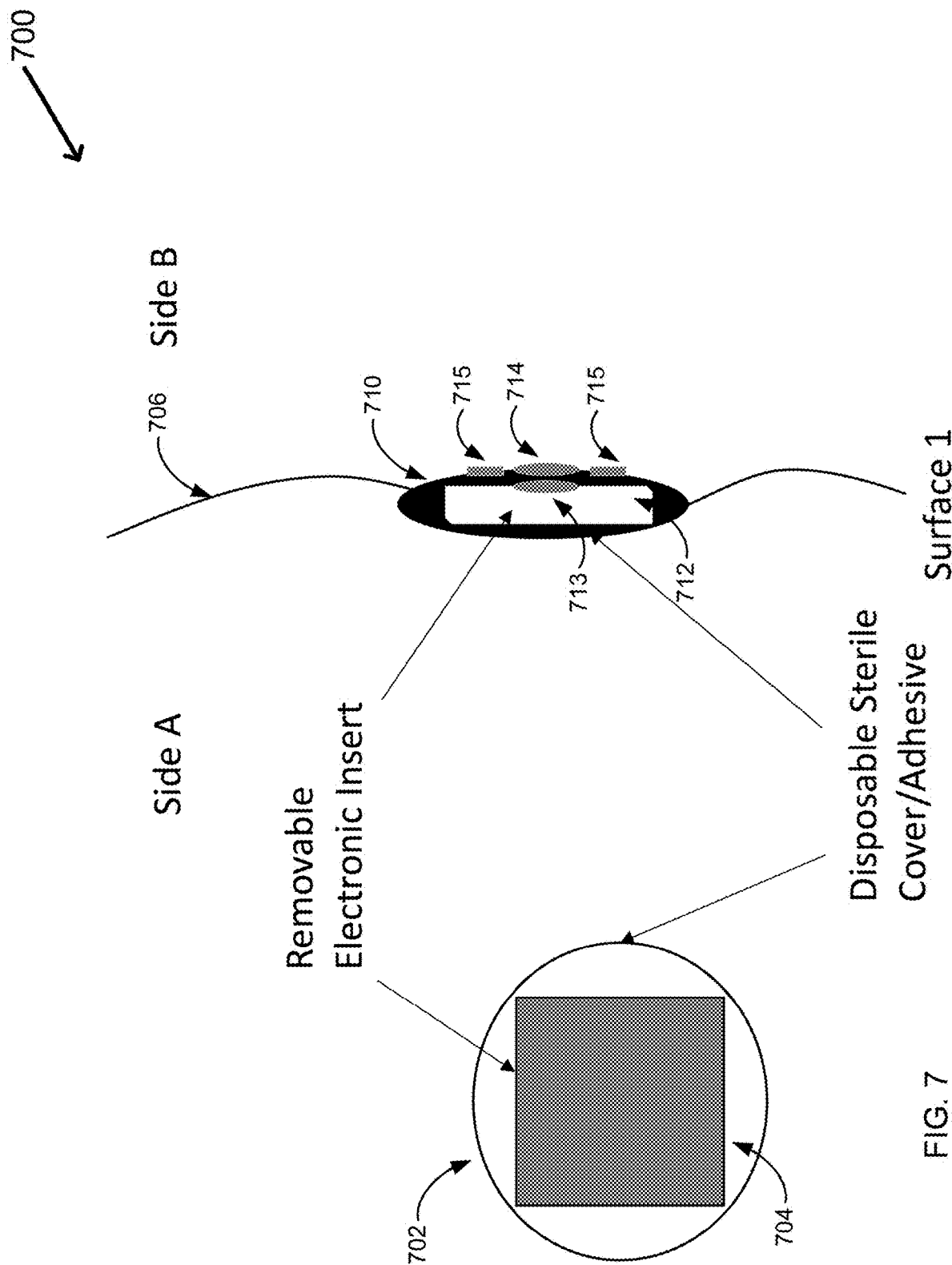
FIG. 7 illustrates an example implementation of a disposable, adhesive cover for SLAM with internal and external ultrasound gel.

FIG. 7 illustrates an example implementation of a disposable adhesive cover for SLAM. Diagram 700 shows an example implementation of a SLAM. A removable electronic insert 704 may be inserted in a disposable cover 702. The disposable cover 702 may have an internal surface prepared with an ultrasound conductive gel 713 and one outer surface treated with a ring of adhesive 715 capturing ultrasound conductive gel 714 to be attached to skin 706. The disposable cover (and the adhesive) may be sterile and medical grade for medical applications.

SLAM designs may be supplied sterile and fully disposable with adhesive and ultrasound conductive gel preapplied. SLAMs may be wired or wireless. SLAMs may contain a battery. SLAMs may be rechargeable. SLAM may be made MRI or CT compatible. SLAM may be modular with a removable component that is not compatible with MR or CT. SLAM technique is applicable to Orthopedic and Spine Surgery with distance to bone measurements, but may be extended for all minimally invasive surgery using the internal coordinate system as a connection to the ideal medical imaging modality being combined in the Navigation System or AR for the surgery planned.

Figure 8:
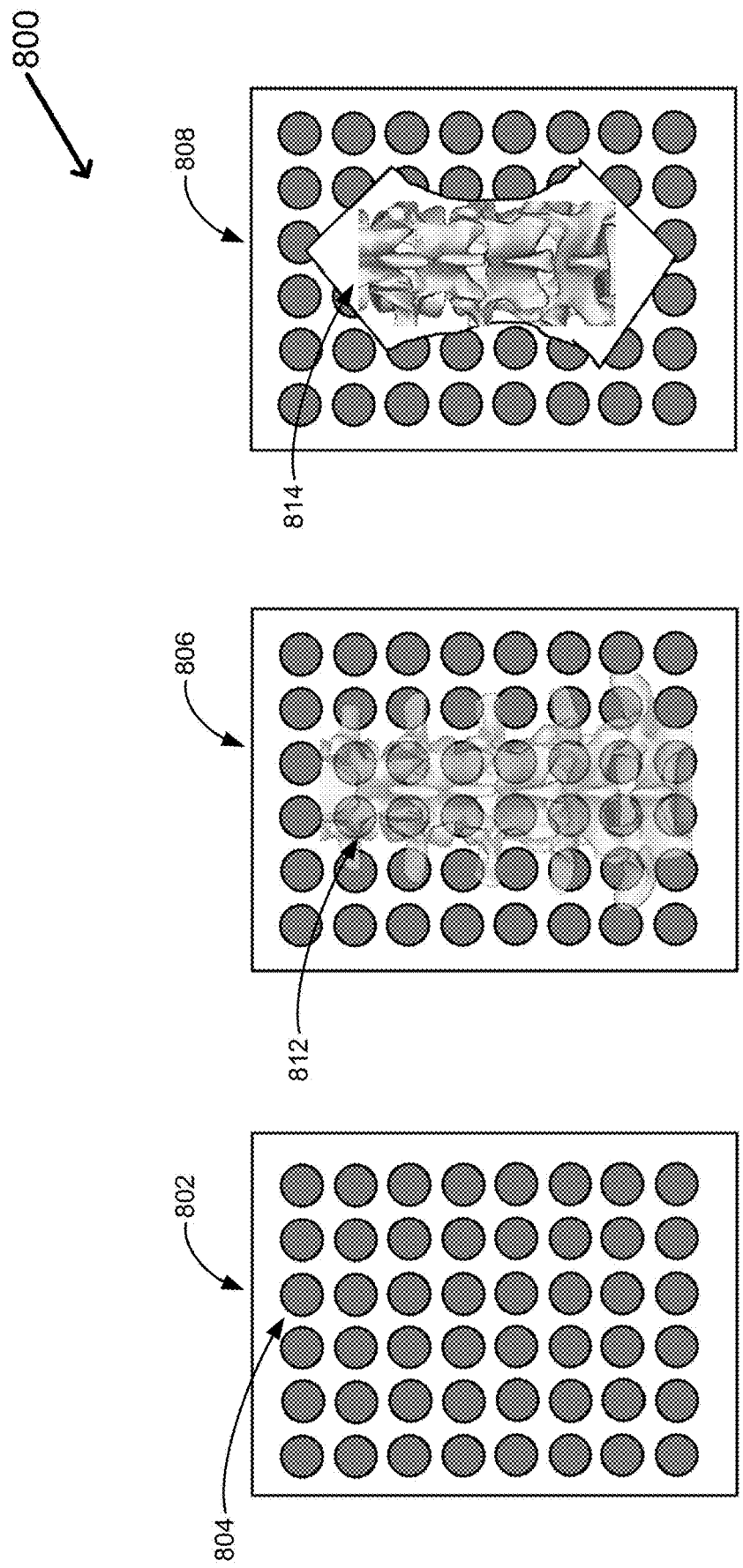
FIG. 8 illustrates an example SLAM sheet and two example surgery implementations.

FIG. 8 illustrates an example SLAM sheet and two example surgery implementations.

Diagram 800 shows another example implementation of SLAMs, in form of sheets. As discussed previously, SLAMs with multiple channels and multiple SLAMs may provide higher accuracy. For SLAMs arranged in a predetermined matrix calculation speeds may be enhanced. An example sheet 802 may include a matrix of SLAMs 804. The sheet may be treated with an adhesive and ultrasound optimized gel to be attached to the patient's skin about the procedure location to provide detection of bone structure profile under the skin. Example sheet 806 shows how AR surgery may be performed through the sheet, where the SLAMs may detect bone structure 812 under the sheet. Since the operation may be performed laparoscopically or through incisions in other parts of the body (e.g., on the sides), the sheet 806 may maintain its integrity. Example sheet 808 shows how open surgery may be performed through a sheet of SLAMs, where part of the sheet 808 may be transected or removed (e.g., torn) and incision made through the transected or removed part. The remaining SLAMs on the sheet may detect the bone structure 814 and help synchronize OR coordinate system and internal coordinate system.

The co-registration of the internal coordinate system and other medical imaging modalities may be performed with conventional fiducials, or image matching techniques, or using SLAM applied during scans. SLAM may self-locate with distance to bone with single or multiple emitter/sensors. SLAMs may be incorporated into a patterned array (e.g. rectilinear) attached to a stick-on sheet. SLAMs may be located within the OR space through a variety of means including but not limited to these techniques used alone or in combination: direct visualization, active light emitter, RF emitter, RF detection (e.g., RFID), acoustic signal.

SLAMs may be located in a 360-degree circumference on the skin of the patient to provide higher resolution information about the inner anatomy. SLAM array may generate distance to key anatomy for all Navigated or AR surgery. SLAM ultrasound or other energy may be focused to optimize accuracy at specific depths of tissue to accommodate patients with different body mass or various anatomy. SLAM focus or angle may be created virtually using phase array and virtual aiming with a group of emitter/sensor elements. Combinations of SLAMs may be used to replace handheld wands for non-surgical and surgical ultrasound methods.

SLAMs may be packaged sterile and in a standby condition that is activated by removal from packaging, or by removal of adhesive backing that may expose ultrasound conductive gel, or any substance meant to improve communication of SLAM signals through the skin. SLAMs may incorporate an indicator light, or lights, or display to show their powered or other status. SLAMs may have a unique optically recognizable pattern that enables automated identification, Unique Device Identifier, location and integration into SLAM data pool. (such as a QR code). SLAMs may self-identify a unique identity through an optical output (flashing light) that communicates to the tracking system or the AR Headset directly or in combination with other communication means such as, but not limited to IR, BT, WiFi, RF, dynamic QR code, etc.

SLAMs may have a 3-dimensional indicator tree that is tracked by the tracking system to provide information about its orientation and position. Number of SLAMs: SLAMs may be used solo, or in combination at user determined locations to match the coordinate systems. The more SLAMs that are used, the more resolution of fit the system may provide. Use of 9-Axis accelerometers may be used to replace conventional 3 ball optical location trees for SLAMs, or in general for navigated instruments, through orientation sensing in addition to inertial location in combination with optical tracking of a single point.

SLAMs may contain single or multiple ultrasound emitter/sensors. It is envisioned that emitters and sensors may be housed in separate physical packages. Fixed multiple emitter/sensors may be prefixed or user aimed at different angles to further poll data from the Internal space. SLAMs may be multiplexed or used as phase arrays. Additional known gross placement information about the SLAM location (e.g. midline posterior Lumbar Spine) may be incorporated to improve accuracy and speed of coordinate system correlation. Collection of data from the SLAM group creates a 3D picture of underlying anatomy that may be matched to preoperative imaging for a 3D through a variety of mathematical techniques. Data from SLAMs may be adjusted to map to known range of motion in order to accommodate the mobility of the bony anatomy across joints or in the case of the spine spine across intervertebral discs.

Different methodologies for location with respect to internal anatomy may include Bounce Back (Electromagnetic Radiation, Ultrasound, Light); Pass Through (Electromagnetic Radiation, X-Rays, Non-ionizing Radiation); Determination with invasion (Percutaneous insertion of sensor(s) or emitter(s) such as into structures e.g. blood vessels, Placed with live X-ray guidance, End of instrument, or Instrument that attaches to an internal anatomy and protrudes to the OR space, and Bodily pathway (X-Ray with radio opaque dye may be introduced either by percutaneous or bodily pathway) insertion of sensor(s) or emitter(s) such as PET or SPECT); and Combinations thereof.

To speed processing and improve accuracy, during calibration the SLAM system may be informed about the general region of application (e.g., Lumbar Spine Medial and Lateral pairs 3" from midline, Thoracic Spine Midline).

SLAM data may be co-registered with other intraoperative imaging data to co-register scans done during the operation: Optionally, information from 3-9-axis accelerometer (acceleration, gyroscopy, and magnetometry) with optional signal fused may be used to provide SLAM location in isolation, or in addition to direct visualization techniques.

Using a Tracking array to monitor position of SLAM units. Using AR Headset to monitor position of SLAM units. Using a combination of Tracking array and AR Headset to monitor position of SLAM units. Wired or wireless. Arrays may be static focused and angled and very small in a pattern. Arrays may incorporate dynamic focus and angle.

A collection of SLAM modules may be used in phased array, digital antenna array. Internal Localizing signal such as but not limited to electromagnetic, mechanical, chemical, thermal, acoustic, optical, ionizing radiation. Return signal from internal structure may be Reflection of same signal or Transformation to modified signal Electromagnetic, etc.

The SLAM array may be used for ultrasound techniques in isolation or in combination in combination with separate Ultrasonography Systems performing methods including but not limited to: Doppler Ultrasound; Contrast Ultrasonography; Molecular Ultrasonography; Elastography (Ultrasound Elastic Imaging); Interventional Ultrasonography; Compression Ultrasonography; or Panoramic Ultrasonography.

SLAM sensor locations in 3D space during procedure may be determined by known methods such as, but not limited, to optical observation with reflectors, RF sensing technologies, active optical emitters, and so forth.

The SLAM array time of flight data is used to achieve pre-operative image and intraoperative coordinate system co-registration through methods that may include one or more of, but are not limited to: Matching fiducial markers from one space to the other; Image data surface fit to SLAM profile determination. Rigid or Non-Rigid Data fitting may be performed in 3 dimensions for the surface profile viewed from the SLAM sensors using one or more in combination of techniques for one or more image modality co-registrations such as but not limited to: Similarity Criteria—feature based or area/volume based; Geometric Transformations (rigid and non-rigid)—similarity, affine, perspective projection, and polynomial models, maximization of suitable statistical similarity measures within a given class (e.g. mutual information). Numeric Optimization—local and global cost optimization, Spatial signal domain, Spatial Fourier frequency domain, Nelder-Mead downhill simplex method, Powell's direction set method, the Levenberg-Marquardt search, and quasi-Newton (variable metric) methods. Image Resampling—Forward resampling, and Backward resampling. Techniques such as, but not limited to deformation registration or Image warping may be used in cases where the anatomy being fitted may be deformed. Co-registration may be performed using AI/ML with or without feature constraints.

SLAM profile and preoperative image data fitting may be performed globally across the entire preoperative image and/or for anatomy where there may be movement of internal anatomy from the original preoperative imaging (spine). SLAM sensors are applicable to adjacent applications such as construction placing screws with Augmented reality to avoid protrusion on blind side. SLAM sensors may be used to create a continuous diagnostic ultrasound capability that may be useful for monitoring during childbirth.

Figure 9A:
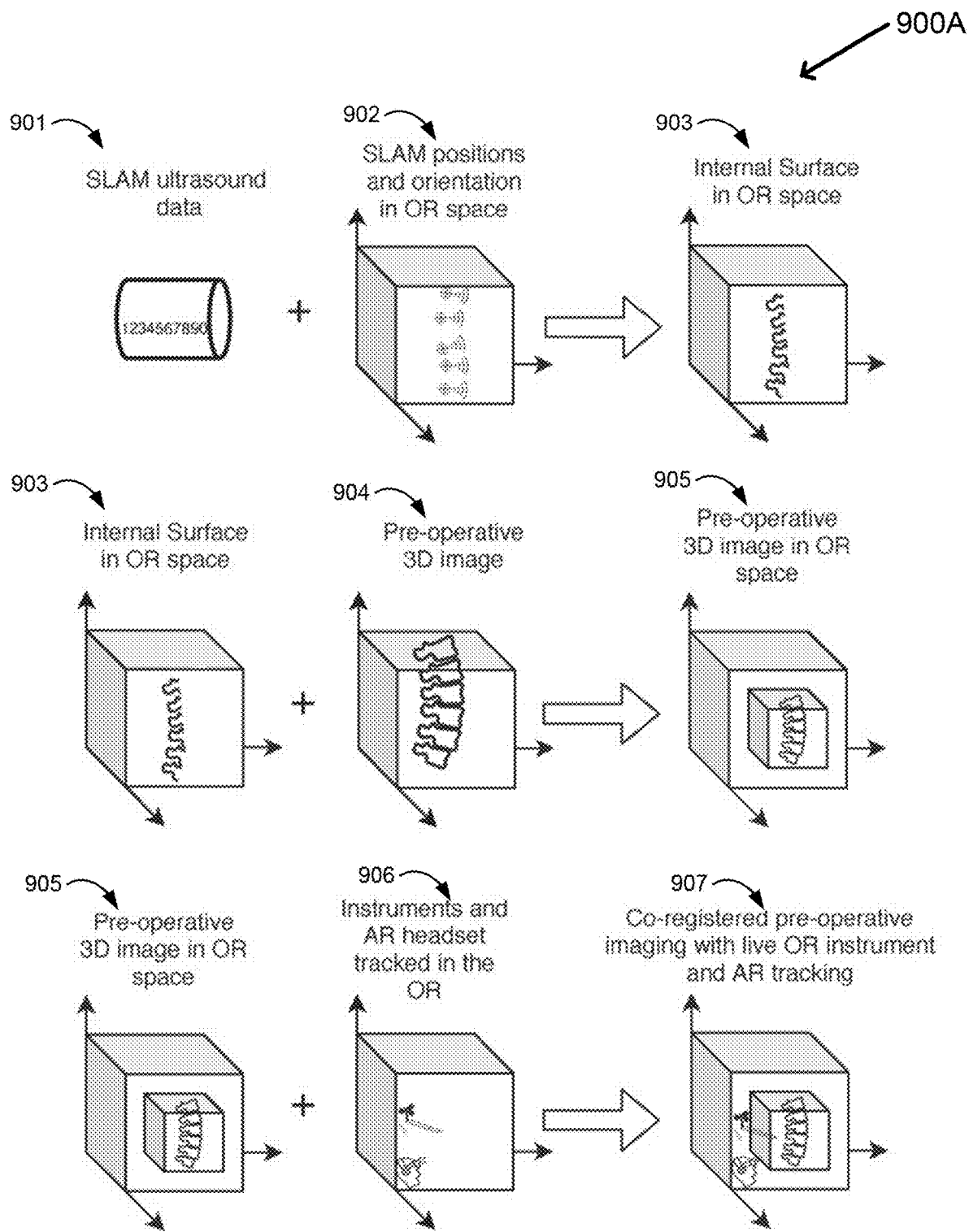
FIGS. 9A and 9B illustrate a qualitative flow of information being computed within the computing device for an operating room embodiment, arranged in accordance with at least some embodiments described herein.
Figure 9B:
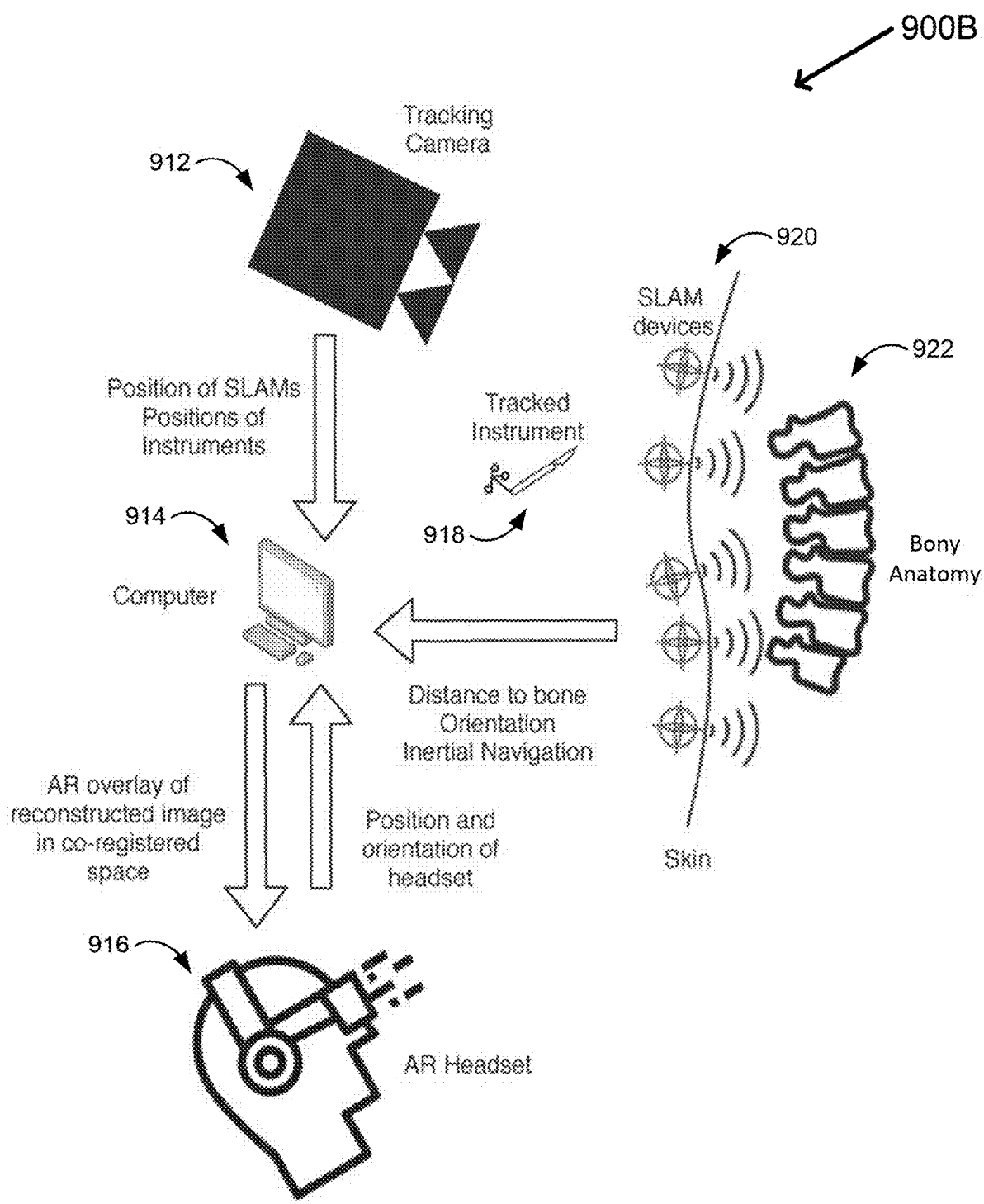

FIGS. 9A and 9B illustrate a qualitative flow of information being computed within the computing device for an operating room embodiment.

Diagram 900A shows a multi-stage process that begins with SLAM ultrasound data (901), which may be combined with SLAM positions and orientation in OR space (902) resulting in internal surface (bone structure) coordinates in OR space (coordinate system) (903). The internal surface in OR space (903) may be combined with a pre-operative image (904) of the bone structure resulting in a pre-operative image in OR space (coordinate system) (905). The pre-operative image in OR space (905) may be combined with instruments and an AR Headset tracked in the OR (906) resulting in co-registered pre-operative imaging with live OR instruments and AR tracking (907).

Diagram 900B shows various components in an OR space such as SLAMs 920 (attached to patient's skin), tracked instrument 918, and AR Headset 916. The positions of these components within the OR coordinate system may be tracked through a number of methods such as accelerometers on those components and/or through visual tracking (by tracking camera 912). A computing device/system 914 may receive the position information from the various components along with distance to bone structure 922 information and combine the information for co-registered pre-operative imaging with live OR instruments and AR tracking.

A "sensing device" as used herein refers to a device such as a SLAM that is affixable to the skin of a patient or an outside surface of an object and sense internal structures (e.g., skeletal anatomy features, soft anatomy features, or object internal features). A sensing device may include a transmitter and a receiver to transmit a non-invasive energy to detect the internal structures, where a portion of the energy reflected from the internal structures may then be detected by the receiver. In some examples, the transmitter and the receiver may be integrated as a transceiver. In other examples, the sensing device may include additional components including, but not limited to, a processor, a memory, an indicator (e.g., an LED indicator), a location detector, etc.

According to some examples, a medical sensing system may include one or more sensing devices, where each sensing device is configured to be affixed on a patient's skin near a procedure site; locate itself with respect to one or more features of internal anatomy of the patient, where the internal anatomy comprises at least skeletal anatomy or soft tissue anatomy; and provide location information with respect to the internal anatomy of the patient for correlation of the internal anatomy with a coordinate space of an operation room.

According to other examples, each sensing device may be configured to utilize a non-invasive probing energy that reflects from the one or more features of the internal anatomy and is then detected by the sensing device. The medical sensing system may further include a computing device configured to employ a tracking system to track real time locations of the one or more sensing devices through one or more of wired or wireless communication with the one or more sensing devices or visual tracking; receive location information from the tracking system; and process the received sensing device location information in combination with the internal anatomy to generate a correlation between locations of the operating room coordinate space and the internal anatomy coordinate space. The computing device may be further configured to utilize the location information with respect to the internal anatomy of the patient to correlate a position of the one or more sensing devices with a medical scan.

According to further examples, the medical sensing system may also include a visualization system configured to receive the processed location information from the computing device; and present a visualization based on internal anatomy information associated with the procedure site to a medical professional along with superimposed visualizations of surgical instruments and implants. The medical sensing system may further include a surgical system configured to receive the processed location information from the computing device; and inform a robotic surgical system. The visualization system may include a wall-mount display, a desktop display, or an augmented reality (AR) display. Each sensing device may include at least an ultrasound transceiver. Each sensing device may include at least an ultrasound transceiver and an accelerometer. Each sensing device may be configured with one or more location sensing channels. The one or more sensing devices may be arranged as a matrix on a sheet to be affixed on the patient's skin about the procedure site.

According to yet other examples, a method for medical sensing may include affixing one or more sensing devices on a patient's skin near a procedure site, where each sensing device locates itself with respect to one or more features of internal anatomy of the patient, and the internal anatomy comprises at least skeletal anatomy or soft tissue anatomy. The method may also include receiving location information, from one or more sensing devices, with respect to the internal anatomy of the patient for correlation of the internal anatomy location with a coordinate space of an operation room.

According to some examples, each of one or more the sensing devices may employ a non-invasive probing energy that reflects from internal structures and is then detected by the sensing device. The method may further include tracking real time locations of the one or more sensing devices through one or more of wired or wireless communication or visual tracking with a tracking system; receiving location information from the tracking system; and processing the received location information to generate a correlation between locations of the internal anatomy of the patient and an operating room coordinate space. The visualization may include spatially synchronized information from positions of the one or more sensing devices with a coordinate space of medical scans.

According to other examples, the method may further include presenting a visualization based on the internal anatomy information associated with the procedure site to a medical professional along with superimposed visualizations of surgical instruments and implants. The method may also include informing a robotic surgical system with location information or processed location information. The visualization system may include a wall-mount display, a desktop display, or an augmented reality (AR) display. Each sensing device may include at least an ultrasound transceiver. Each sensing device may be configured to locate itself through at least an accelerometer and an ultrasound transceiver. Tracking the real time locations of the one or more sensing devices may include receiving location information through one or more location sensing channels. Affixing the one or more sensing devices on the patient's skin may include arranging the one or more sensing devices as a matrix on a sheet to be affixed on the patient's skin around the procedure site.

According to further examples, a sensing system may include one or more sensing devices, each sensing device configured to be affixed on a surface of an object, wherein the surface is movable in an unpredictable manner with respect to an internal structure or another surface of the object; locate itself with respect to one or more of the internal structures of the object; and provide location information with respect to the internal structures for correlation of its spatial coordinate space with a spatial coordinate space of the internal structure of the object. The sensing system may also include a tracking system configured to track real time locations of the one or more sensing devices through one or more of wired or wireless communication with the one or more sensing devices or visual tracking. The sensing system may further include a computing device configured to receive location information from the tracking system and sensing devices; and process the received location information for generation of the correlation of the sensing device's spatial coordinate space with a spatial coordinate space of the internal structure or the other surface of the object.

According to yet other examples, the visualization may include spatially synchronized information from the coordinate space of the sensors and the coordinate space of internal structures determined through a secondary means. The sensing system may further include a visualization system configured to receive the processed location information from the computing device; and present a visualization based on internal structure or surface structure information associated with the object. The sensing system may also include a deployment system configured to receive the processed location information from the computing device; and utilize the information based on internal structure or surface structure information associated with the object.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only and is not intended to be limiting.

The herein described subject matter sometimes illustrates different components contained within, or connected with, different other components. Such depicted architectures are merely examples, and in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to,"

the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. A medical sensing system comprising:
   a plurality of sensing devices, wherein the sensing devices are arranged as a matrix on a sheet to be affixed on a patient's skin about a procedure site via an adhesive, each sensing device comprising a multi-axis accelerometer and an ultrasound transducer;
   an optical tracking system comprising a camera positionable to observe the sensing devices; and
   a computing device operatively connected to the sensing devices and the optical tracking system;
   wherein each sensing device is configured to locate itself, using at least the ultrasound transducer, with respect to one or more features of internal anatomy of the patient to provide first location information to the computing device with respect to the internal anatomy of the patient, wherein the internal anatomy comprises at least skeletal anatomy or soft tissue anatomy;
   wherein the optical tracking system is configured to provide, to the computing device, second location information of the sensing devices with respect to a coordinate space of an operation room; and
   wherein the computing device correlates the internal anatomy with the coordinate space and preoperative imaging.

2. The medical sensing system of claim 1, wherein for each sensing device, the sensing device is configured to utilize a non-invasive probing energy that reflects from the one or more features of the internal anatomy and is then detected by the sensing device.

3. The medical sensing system of claim 1, further comprising a display operatively connected to the computing device, wherein the computing device causes the display to show the internal anatomy and at least one of (a) the preoperative imaging superimposed with the internal anatomy or (b) superimposed visualizations of surgical instruments and implants.

4. The medical sensing system of claim 3, wherein the display comprises a wall-mount display, a desktop display, or an augmented reality (AR) display.

5. The medical sensing system of claim 1, further comprising:
   a robotic surgical system configured to:
      receive the processed location information from the computing device to inform the robotic surgical system.

6. The medical sensing system of claim 1, wherein each sensing device is configured with one or more location sensing channels.

7. A method for medical sensing, the method using the system of claim 1, the method comprising:
   for at least one sensing device of the sensing devices, sensing the first location information using the ultrasound transducer;
   receiving, in the computing device, the second location information;
   receiving, in the computing device, fest third location information of the at least one sensing device from the multi-axis accelerometer in the at least one sensing device, wherein the third location information relates to a position of the at least one sensing device in the coordinate space; and
   using the computing device, the second location information, and the third location information, correlating the first location information with the coordinate space.

8. The method of claim 7, further comprising displaying a profile of the internal anatomy and at least one of (a)

preoperative imaging superimposed with the internal anatomy or (b) superimposed visualizations of surgical instruments and implants.

9. The method of claim 8, wherein the displaying comprises displaying on a wall-mount display, a desktop display, or an augmented reality (AR) display.

10. The method of claim 7, further comprising:
displaying a profile of the internal anatomy and each of (a) preoperative imaging superimposed with the internal anatomy and (b) superimposed visualizations of surgical instruments and implants.

11. The method of claim 7, further comprising:
informing a robotic surgical system with data from the ultrasound transducer.

12. The method of claim 7, wherein sensing the first location information comprises using multiple sensing devices.

13. The system of claim 1, wherein, for each sensing device, the sensing device comprises a plurality of ultrasound transducers carried by the sensing device.

14. A sensing system comprising:
a plurality of sensing devices arranged as a matrix on a sheet, wherein each sensing device comprises at least one multi-axis accelerometer and at least one ultrasound transducer;
an optical tracking system comprising a camera positionable to observe at least one sensing device of the plurality of sensing devices; and
a computing device operably coupleable to the optical tracking system and the at least one sensing device; wherein:
(i) the sensing devices are affixable on a surface of an object via an adhesive, wherein the surface is movable with respect to an internal structure of the object;
(ii) the at least one sensing device is configured to communicate ultrasound data from the at least one ultrasound transducer with respect to the internal structures of the object and to communicate accelerometer data from the accelerometer regarding first location information of the sensing device with respect to a coordinate space;
(iii) the optical tracking system is configured to observe the at least one sensing device to track the at least one sensing device, and to generate second location information of the at least one sensing device with respect to the coordinate space; and
(iv) the computing device is configured to receive the ultrasound data, the first location information, and the second location information, and to:
(a) process the ultrasound data and the first location information to determine a first correlation of the internal structure of the object with the coordinate space;
(b) process the first location information and not the second location information to determine a second correlation of the internal structure of the object with the coordinate space; and
(c) cause a visualization system to present a spatially synchronized visualization of the internal structure of the object or of the surface structure of the object based on the first correlation or the second correlation.

15. The sensing system of claim 14, further comprising:
a visualization system configured to present the visualization.

16. The sensing system of claim 14, further comprising a display operatively connectable to the computing device, wherein the computing device causes the display to show the internal structure and at least one of (a) a preoperative imaging superimposed with the internal structure or (b) a superimposed visualization of a surgical instrument.

* * * * *

UNITED STATES PATENT AND TRADEMARK OFFICE
CERTIFICATE OF CORRECTION

| | | |
|---|---|---|
| PATENT NO. | : 12,369,987 B2 | Page 1 of 1 |
| APPLICATION NO. | : 17/228841 | |
| DATED | : July 29, 2025 | |
| INVENTOR(S) | : Dennis Chien | |

It is certified that error appears in the above-identified patent and that said Letters Patent is hereby corrected as shown below:

On the Title Page

Item (57), in Column 2, in "Abstract", Line 9, delete "SLAMS" and insert -- SLAMs --.

In the Claims

In Column 14, Line 57, in Claim 7, after "device," delete "fest".

Signed and Sealed this
Eighteenth Day of November, 2025

John A. Squires
*Director of the United States Patent and Trademark Office*